United States Patent [19]

Calari

[11] Patent Number: 4,493,691
[45] Date of Patent: Jan. 15, 1985

[54] DEVICE FOR PERFORMING PLASMAPHERESIS BY CENTRIFUGATION

[75] Inventor: Alessandro Calari, Mirandola, Italy

[73] Assignee: Dideco S.P.A., Mirandola, Italy

[21] Appl. No.: 474,925

[22] Filed: Mar. 14, 1983

[30] Foreign Application Priority Data

Mar. 25, 1982 [IT] Italy .................. 20399 A/82

[51] Int. Cl.³ .................................. B04B 15/00
[52] U.S. Cl. ........................ 494/10; 422/72; 494/21; 494/45
[58] Field of Search .............. 494/10, 11, 1, 21, 45, 494/18; 422/72, 64; 604/4, 5, 6

[56] References Cited

U.S. PATENT DOCUMENTS

| | | | |
|---|---|---|---|
| 3,999,862 | 12/1976 | Revillet | 494/10 |
| 4,244,513 | 1/1981 | Fayer | 494/11 |
| 4,279,862 | 7/1981 | Bretaudiere | 422/72 |
| 4,285,810 | 8/1981 | Kirkland | 494/10 |
| 4,350,283 | 9/1982 | Leonian | 422/72 |

Primary Examiner—Robert W. Jenkins
Attorney, Agent, or Firm—Guido Modiano; Albert Josif

[57] ABSTRACT

The device comprises a rotor formed with a circumferential groove including a widening with an apertured bottom whereat two monitoring stroboscopes are arranged, the groove being provided for engaging with the red cell and plasma exit end of a disposable bag, the other end whereof is so designed and arranged as to receive whole blood.

6 Claims, 5 Drawing Figures

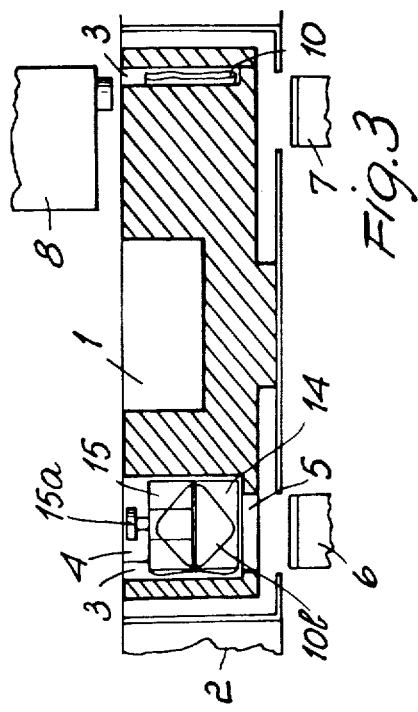
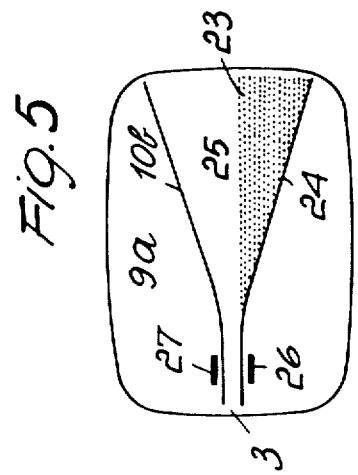
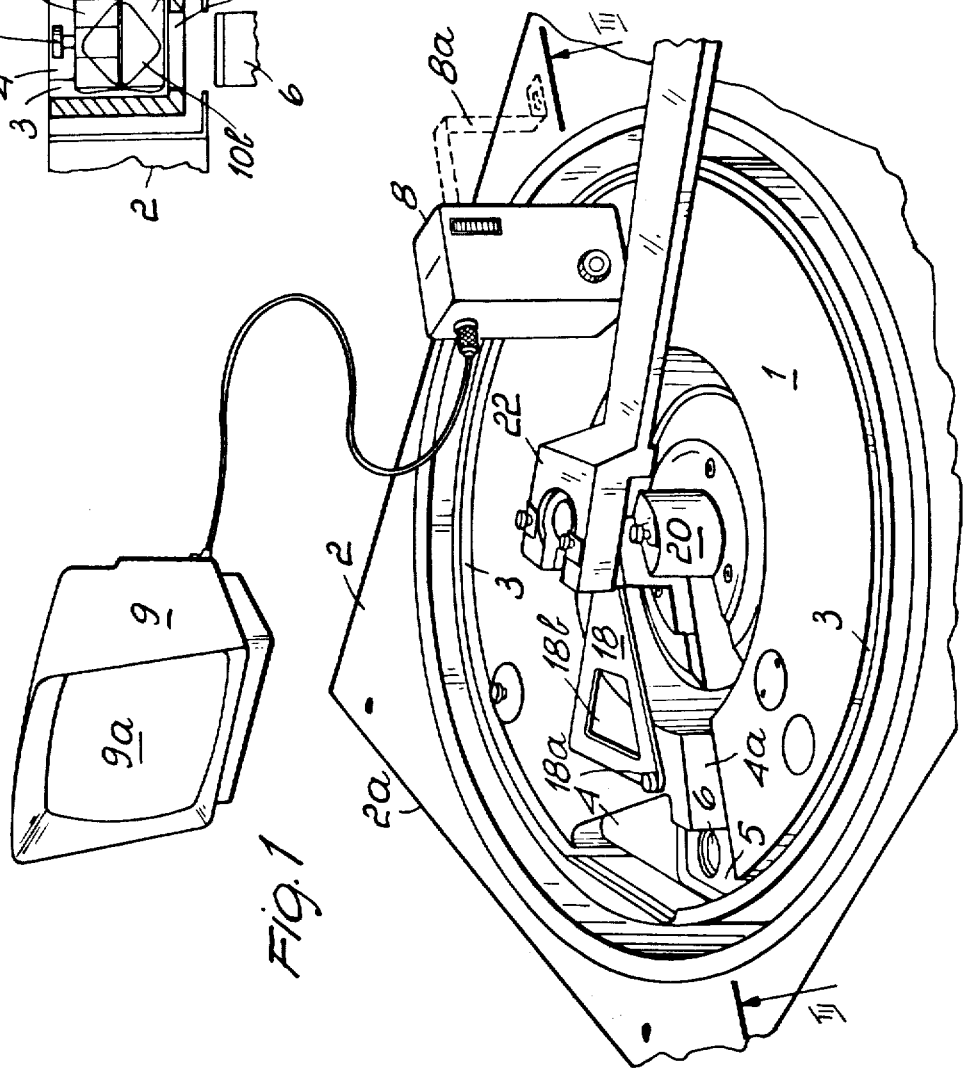

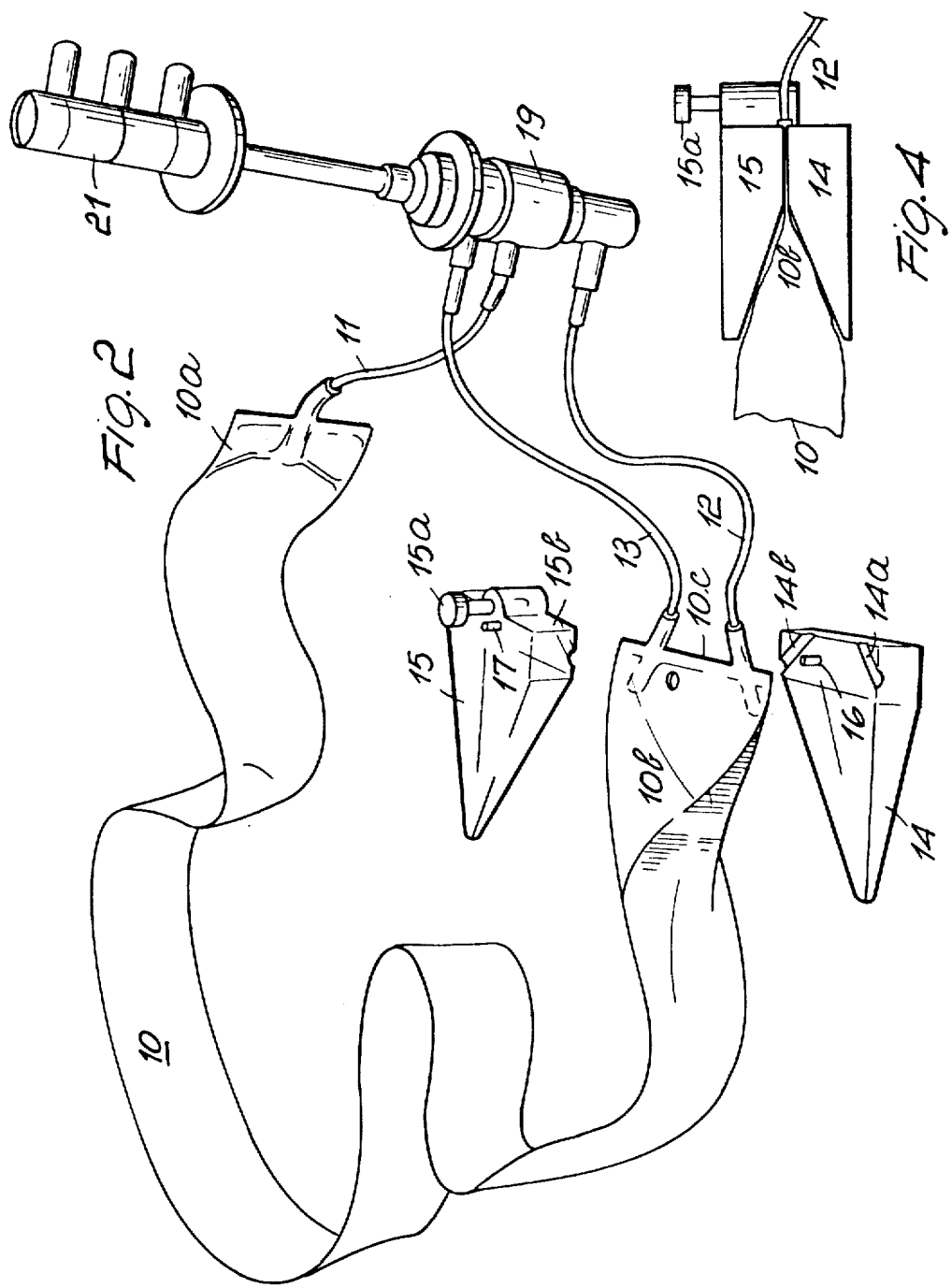

DEVICE FOR PERFORMING PLASMAPHERESIS BY CENTRIFUGATION

BACKGROUND OF THE INVENTION

This invention relates to a device for performing plasmapheresis by centrifugation.

It is known that several plasmapheresis devices have been proposed i.e. devices performing separation of plasma from red cells in blood extracted from a patient or a donor by centrifugation of the blood, utilizing the different specific gravity of the two components.

With such devices, it is evidently highly important that the operator be allowed to apply a highly accurate control on the process progress, in order for the same to always proceed in optimum conditions, and, from this point of view, it must be said that conventional devices leave much to be desired.

SUMMARY OF THE INVENTION

It is an object of this invention to provide a centrifugation plasmapheresis device, whereby the operation in progress can be monitored at any moment and with a high degree of accuracy.

A further object of the invention is to provide such a device, whereby the plasmapheresis process can be monitored without fatiguing by one, and possibly several, operators.

These objects are achieved by a device for performing plasmapheresis by centrifugation, according to the invention, including a body, a rotor rotatably supported by said body and having at its center a support for a connector coupling of the type including a stationary connector block and a rotary connector block in rigid rotatory relationship with the rotor and wherefrom the conveying lines for whole blood, red cells, and plasma extend, characterized in that it comprises, supported on said body a TV camera defining an optical axis and connected to a TV display, formed on said rotor, a circumferential groove with a widening adapted to accommodate a bag which receives whole blood at one end, and having, at the other end, a substantially tetrahedral shape and being accommodated in the space portion defined between two blocks of a transparent material removably inserted in said widening, and provided with two lines extending substantially from the ends of the horizontally laid bottom for letting out red cells and plasma, respectively, below said rotor there being provided two stroboscopic flash lights located to face a circular path followed during rotation of said rotor by an opening provided in the rotor through the bottom of said widening, one of said stroboscopic flash lights being arranged at the machine front and the other at any position spaced therefrom and overlaid by said TV camera and in alignment with said optical axis thereof, said optical axis intersecting said path.

Advantageously, the TV screen is provided with two reference marks adapted to visually identify the maximum allowable amplitude of the red cells-plasma interface.

BRIEF DESCRIPTION OF THE DRAWINGS

Further features and advantages will be more clearly apparent from the following description of a preferred, though not limitative, embodiment of the invention, as illustrated by way of example and not of limitation in the accompanying drawings. where:

FIG. 1 is a perspective view of the device without the bag intended for containing the blood and the transparent material blocks;

FIG. 2 shows the bag intended for containing the blood, and the transparent material blocks;

FIG. 3 shows diagrammatically a diametrical cross-section of the device along line III—III of FIG. 1 with the bag inserted in the rotor, ready to operate;

FIG. 4 shows how the tetrahedral-shape end of the bag is inserted between the blocks of a transparent material; and FIG. 5 shows the image to be obtained on the TV display screen during the normal operation of the device.

DESCRIPTION OF THE PREFERRED EMBODIMENTS

With reference to the drawing figures, indicated at 1 is the rotor accommodated in the body 2 of the device. The rotor is provided with a circumferential groove 3 which opens in a recess or widening 4 at the bottom of which the opening 5 is formed; facing the circular path followed by this opening during rotation of the rotor 1, there are provided in the device body below the rotor 1 two stroboscopic flash lights 6 and 7, the former of which is located at the front 2a of the device, and the latter is overlaid by the TV camera 8, supported, in any known manner, e.g. by an adjustable bracket, diagrammatically indicated at 8a in dotted lines on the body 2 and connected to the the TV display 9 having a screen 9a normally located in the proximities of the device. The TV camera 8 has an optical axis intersecting the circular path followed, during rotation of the rotor by the opening 5 and in alignment with the stroboscope 7.

Intended for insertion into the groove 3 of the rotor is the disposable bag 10 which receives whole blood through the line 11 at its end 10a, and is shaped as a tetrahedron 10b at the other end, where, at the ends of the bottom 10c, there are connected the lines 12 and 13 for conveying red cells and plasma, respectively; in inserting the bag 10 into the groove 3, said tetrahedrally shaped end 10b is intended, as shown particularly in FIGS. 3 and 4, for accommodation in the space portion delimited by the two blocks 14 and 15 formed from a transparent material, which are inserted to size in the recess 4 such that the bottom 10c can take a substantially horizontal lay.

Between the lower block 14, which may be slightly dulled to attenuate the light from the stroboscopic flash light and is provided with the small channels 14a and 14b for the passage of the lines 12 and 13, and the upper block 15, which is provided with the handhold knob 15a and is also provided with small channels such as 15b at those in the block 14, there is arranged the locating peg formed by the male member 16-female member 17 coupling for the correct mutual positioning.

When the bag 10 is inserted in the groove 3, it assumes the circumferential shape all around and the end 10a reaches the recess 4 from the opposite side with respect to the end 10b, the connection lines 11, 12, 13 passing through the radial slot 4a provided in the rotor 1, for connection with the rotary connector 19.

On completion of the positioning, a rotatable small plate 18 provided on the rotor 1 is rotated about the pin 18a to move into a position overlying the blocks, thereby it can be assured that the same are held in position; said small plate 18 is provided with a large cutout 18b at the area intended to overlap the tetrahedron 10b.

It will be understood that the lines 11 for the whole blood, 12 for the red cells, and 13 for the plasma, are conducted conventionally to the rotary connector block 19, inserted in the support 20 provided at the rotor center, the connector unit also comprising a stationary connector block 21, secured to the arm 22 which extends from the body 2 of the device supported on a stationary part of the device. From the outlets of the stationary connector block 21, said fluids reach the stationary parts of the device. At the start of a plasmapheresis treatment, the bag 10 is inserted into the groove 3 by resting the tetrahedron 10b onto the block 14 and tightening it by superimposition of the block 15 and closure of the small plate 18.

After starting the rotation of the rotor, the blood begins to be centrifuged and reaches the bag 10 from the line 11 with separation of the red cells, which move to the periphery, from plasma: the process takes place all along the bag extension and the position of the red cells-plasma interface, which may vary owing to temperature variations or changed conditions of the disposable lines, can be checked in the tetrahedron 10b, directly ahead of the outlet from the bag 10 respectively of the red cells from the line 12 and of the plasma from the line 13, both by direct observation of the stroboscope 6, and through the TV camera 9 on the stroboscope 7, both evidently set for a flashing rate coinciding with that of passage of the tetrahedron 10b thereabove.

Direct monitoring on the stroboscope 6 is normally reserved for the starting stage, it being afterwards advantageous, for the purpose of a good accuracy of monitoring, to make use of the display on the screen 9a: it is in fact possible to check thereon, as shown in FIG. 5, that the interface 23 between the red cells 24 and plasma 25 remains within the field delimited by the reference marks 26 and 27 which identify the maximum allowable amplitude for an optimal operation of the device.

The display on the screen 9a is moreover less fatiguing for the operator's eyes than direct observation of the stroboscope 6, and affords the added advan. ge of being accessible to several persons.

If the interface 23 reaches one of the reference marks 26 and 27, the operator, possibly warned by an alarm device which may be actuated by feelers provided as reference marks, will act on the device control members to restore the optimum conditions; it is also contemplated that said alarm device be connected to a circuit of self-control of the interface position, so as to remove the need for the operators' intervention.

The invention described is susceptible to many modifications and variations, all falling within the scope of this inventive concept; moreover, all of the details may be replaced with other, technically equivalent, elements.

In practicing the invention, the materials used, and the shapes and dimensions, may be any suitable ones to meet individual requirements.

I claim:

1. A device for performing plasmapheresis by centrifugation, comprising a body, a rotor rotatably supported by said body and having at its center a support for a connector coupling of the type including a stationary connector block and a rotary connector block in rigid rotatory relationship with the rotor and wherefrom the conveying lines for whole blood, red cells, and plasma extend, supported on said body, a TV camera defining an optical axis, and connected to a TV display, formed on said rotor, a circumferential groove with a widening adapted to accommodate a bag which receives whole blood at one end, and having, at the other end, a substantially tetrahedral shape and being accommodated in the space portion defined between two blocks of a transparent material removably inserted in said widening, and provided with two lines extending substantially from said other end for letting out red cells and plasma, respectively, below said rotor there being provided two stroboscopic flash lights located to face a circular path followed during rotation of said rotor by an opening provided in the rotor through the bottom of said widening, one of said stroboscopic flash lights being arranged at the machine front and the other at any position spaced therefrom and overlaid by said TV camera and in alignment with said optical axis thereof, said optical axis intersecting said circular path.

2. A device according to claim 1, characterized by the provision, on the TV display screen, of two reference marks adapted to visually identify the range of maximum allowable amplitude of the red cells-plasma interface.

3. A device according to claims 1 or 2, characterized by the provision of a warning signal activated upon the red cells-plasma interface reaching one of the extreme positions identified by the reference marks on the TV display screen.

4. A device according to claims 1 or 2, characterized in that the warning signal is connected to a circuit adapted to arrange for self-control of the position of the red cells-plasma interface.

5. A device according to claim 1, characterized in that, between the lower transparent block, as slightly dimmed, and the upper one, having a handhold knob, there is provided a reference for correct mutual positioning.

6. A device according to claim 1, characterized by the provision of a small plate hinge connected to the rotor, adapted to overlap the widening of the circumferential groove and having a cutout at the area corresponding to the tetrahedron shaped end of the bag.

* * * * *